United States Patent
Spears

(10) Patent No.: US 6,344,489 B1
(45) Date of Patent: *Feb. 5, 2002

(54) STABILIZED GAS-ENRICHED AND GAS-SUPERSATURATED LIQUIDS

(75) Inventor: J. Richard Spears, Bloomfield Hills, MI (US)

(73) Assignee: Wayne State University, Detroit, MI (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 54 days.

This patent is subject to a terminal disclaimer.

(21) Appl. No.: 08/581,019

(22) Filed: Jan. 3, 1996

Related U.S. Application Data

(63) Continuation-in-part of application No. 08/273,652, filed on Jul. 12, 1994, now Pat. No. 5,569,180, which is a continuation-in-part of application No. 08/152,589, filed on Nov. 15, 1993, now Pat. No. 5,407,426, which is a continuation-in-part of application No. 07/818,045, filed on Jan. 8, 1992, now Pat. No. 5,261,875, which is a continuation of application No. 07/655,078, filed on Feb. 14, 1991, now Pat. No. 5,086,620.

(51) Int. Cl.[7] .............................. B01J 13/00; B01J 3/00; A61M 1/14; A61M 37/00
(52) U.S. Cl. ...................... 516/10; 422/45; 422/120; 604/23; 604/24; 604/280; 261/107; 261/116
(58) Field of Search ...................... 604/23, 24, 280; 422/45, 120; 62/46.3, 46.1; 261/100, 107, 116, DIG. 28, DIG. 7; 252/186.25, 305, 306, 307; 516/10, 9

(56) References Cited

U.S. PATENT DOCUMENTS

| | | | | |
|---|---|---|---|---|
| 3,862,715 A | * | 1/1975 | Remenyik | 494/22 |
| 3,963,503 A | | 6/1976 | Mackenzie | 106/40 V |
| 4,041,180 A | | 8/1977 | Wilson | 426/11 |
| 4,445,886 A | * | 5/1984 | Osterholm | 604/28 |
| 4,664,680 A | | 5/1987 | Weber | 261/36.1 |
| 4,808,378 A | * | 2/1989 | Nakanishi et al. | 422/48 |
| 4,865,836 A | | 9/1989 | Long, Jr. | 424/5 |
| 4,874,509 A | | 10/1989 | Bullock | 210/169 |
| 4,927,623 A | | 5/1990 | Long, Jr. | 424/5 |
| 4,963,130 A | * | 10/1990 | Osterholm | 604/24 |
| 4,965,022 A | | 10/1990 | Litz | 261/36.1 |

(List continued on next page.)

Primary Examiner—Joseph D. Anthony
(74) Attorney, Agent, or Firm—Margaret A. Kivinski

(57) ABSTRACT

A gas-enriched liquid delivered at a site of interest that is substantially bubble free after delivery into a lower pressure liquid or gas environment. The delivered gas-enriched liquid is produced by a process comprising the steps of:

a) preparing a mixture of gas and liquid;

b) compressing the mixture to a pressure such that the gas completely dissolves in the liquid to form a gas-enriched liquid;

c) enclosing the gas-enriched liquid within a confined space while retaining substantially the same pressure. The confined space has at least one dimension less than about 0.2 mm, and has at least one opening to a liquid or gas environment site of interest having a lower pressure than that of the pressure of the confined space; and d) delivering the gas-enriched liquid from the confined space out through the at least one exit opening to the lower pressure environment without formation of bubbles.

52 Claims, 5 Drawing Sheets

U.S. PATENT DOCUMENTS

| | | | |
|---|---|---|---|
| 4,973,558 A | 11/1990 | Wilson et al. | 435/400 |
| 5,029,579 A * | 7/1991 | Trammell | 128/205.26 |
| 5,072,739 A * | 12/1991 | John | 128/897 |
| 5,080,885 A | 1/1992 | Long, Jr. | 424/5 |
| 5,084,011 A * | 1/1992 | Grady | 604/24 |
| 5,108,662 A * | 4/1992 | Litz et al. | 261/16 |
| 5,261,875 A | 11/1993 | Spears | 604/24 |
| 5,324,436 A | 6/1994 | John et al. | 210/638 |
| 5,344,393 A | 9/1994 | Roth et al. | 604/4 |
| 5,393,513 A | 2/1995 | Long, Jr. | 424/5 |
| 5,407,426 A * | 4/1995 | Spears | 4/24 |
| 5,527,962 A | 6/1996 | Pavia et al. | 564/152 |
| 5,562,608 A | 10/1996 | Sekins et al. | 604/20 |
| 5,569,180 A * | 10/1996 | Spears | 604/24 |
| 5,735,934 A * | 4/1998 | Spears | 75/414 |
| 5,797,874 A * | 8/1998 | Spears | 604/24 |
| 6,030,357 A * | 2/2000 | Daoud et al. | 604/26 |

* cited by examiner

STABILIZED GAS-ENRICHED AND GAS-SUPERSATURATED LIQUIDS

CROSS-REFERENCE TO RELATED APPLICATIONS

This application is a continuation-in-part of application Ser. No. 08/273,652, filed Jul. 12, 1994 now U.S. Pat. No. 5,569,180, which in turn is a continuation-in-part of application Ser. No. 08/152,589, filed Nov. 15, 1993, now U.S. Pat. No. 5,407,426, which in turn is a continuation-in-part of application Ser. No. 07/818,045, filed Jan. 8, 1992, now U.S. Pat. No. 5,261,875, which in turn is a continuation of application Ser. No. 07/655,078, filed Feb. 14, 1991, now U.S. Pat. No. 5,086,620. Each of these disclosures is incorporated by reference herein.

BACKGROUND OF THE INVENTION

1. Technical Field

This invention relates to a new stabilized form of gas-enriched liquid produced by a process comprising generally the steps of: preparing a mixture of a gas and a liquid; compressing the mixture so that the gas completely dissolves in the liquid to form a gas-enriched liquid either before or after enclosing the mixture in a confined space.

2. Description of Background Art

The maximum concentration of gas achievable in a liquid ordinarily is governed by Henry's Law. At ambient pressure, the relatively low solubility of many gases, such as oxygen or nitrogen, within a liquid such as water produces a low concentration of the gas in the liquid. However, there are many applications wherein it would be advantageous to employ a gas concentration within the liquid which greatly exceeds its solubility at ambient pressure. Compression of a gas/liquid mixture at a high pressure can be used to achieve a high dissolved gas concentration, but disturbance of a gas-supersaturated liquid by attempts to eject it into a 1 bar environment from a high pressure reservoir ordinarily results in cavitation inception at or near the exit port. The rapid evolution of bubbles produced at the exit port vents much of the gas from the liquid, so that a high degree of gas-supersaturation no longer exists in the liquid at ambient pressure outside the high pressure vessel. In addition, the presence of bubbles in the effluent generates turbulence and impedes the flow of the effluent beyond the exit port.

U.S. Pat. No. 4,664,680 relates to enriching the oxygen content of water. That reference discloses a number of conventional types of apparatus that can be used for continuously contacting liquid and oxygen-containing gas streams to effect oxygen absorption. To avoid premature liberation of dissolved oxygen before it is incorporated within the bulk of matter to be enriched in oxygen content, pressurizable confined flow passageways are used.

Other oxygen saturation devices are disclosed in U.S. Pat. Nos. 4,874,509; and 4,973,558. These and other approaches leave unsolved the need to infuse gas enriched fluid solutions from a high pressure reservoir toward a reaction site at a lower pressure without cavitation or bubble formation in the effluent at or near the exit port.

SUMMARY OF THE INVENTION

In a co-pending application Ser. No. 152,589, filed Nov. 15, 1993 now U.S. Pat. No. 5,407,426, a method is described for the stabilization of a stream of oxygen-supersaturated water which permitted ejection of the stream from a high pressure vessel into a 1 bar environment without cavitation inception in the effluent at or near the exit port(s). An effluent of water containing oxygen at a concentration as high as on the order of 4 cc oxygen/g of injectate, representing a partial pressure of approximately 140 bar of the dissolved gas, can be ejected from a high pressure vessel into a 1 bar liquid environment with complete absence of cavitation inception in the ejected stream. In air at 1 bar, cavitation inception in a high velocity stream is delayed until breakup of the ejected stream into droplets.

The absence of cavitation inception in water supersaturated with oxygen at a high concentration permits its in vivo infusion into either venous or arterial blood for the purpose of increasing the oxygen concentration of blood without incurring the formation of bubbles which would otherwise occlude capillaries.

In addition to this application as previously described, a wide variety of other applications would benefit from ejection of a gas-supersaturated fluid from a high pressure reservoir into an ambient pressure environment in a manner which is unassociated with cavitation inception at or near the exit port. For example, organic material and plant waste streams, e.g., paper mills and chemical plants, often require an increase in dissolved oxygen content before the discharge of such waste streams in a body of water. U.S. Pat. No. 5 4,965,022 also recognizes that a similar need may also occur at municipal waste treatment plants and that fish farms require increased dissolved oxygen levels to satisfy the needs of high density aquaculture. Other applications are disclosed in my U.S. Pat. No. 5,261,875.

A method is described for ejection of gas-supersaturated fluids or liquids from a high pressure reservoir to a relatively low pressure environment, including ambient pressure, which permits the use of the gas-supersaturated liquid at the lower pressure without immediate cavitation inception. Cavitation nuclei in the liquid are removed by compression in a high pressure reservoir. The use of suitable channels at the distal end of the system for delivery of the gas-supersaturated liquid, plus elimination of cavitation nuclei along the inner surface of the channels, allow ejection of the liquid into a relatively low pressure environment without cavitation inception at or near the exit port.

Thus, an important aspect of the invention described herein is the use of capillary channels at the distal end of the delivery system, along with initial hydrostatic compression of a liquid to remove cavitation nuclei along the inner surface of the channels. When such nuclei contain a relatively insoluble gas, such as oxygen or nitrogen, a hydrostatic pressure of 0.5 to 1.0 kbar is highly effective for this purpose. For nuclei of a soluble gas, such as carbon dioxide, a lower hydrostatic pressure can be used for their dissolution. Cavitation nuclei and bubbles in the bulk liquid are removed in the high pressure reservoir by either direct hydrostatic compression, for example, from movement of a liquid or piston driven by a hydraulic compressor, or by compression from a source of gas maintained at a pressure which would provide the desired concentration of gas in the liquid. Hydrostatic compression to 0.1 to 1.0 kbar rapidly removes cavitation nuclei and bubbles from the liquid, but much lower pressures from a gas source are also effective, although requiring longer periods of time. When a gas source is used to both pressurize the liquid and achieve a desired concentration of a relatively insoluble gas in the liquid, the range of gas pressure would typically be in the 10 bar to 150 bar range. When a highly soluble gas, such as carbon dioxide is used, a lower gas pressure, in the range of 2 to 8 bar would typically be employed to achieve a dissolved gas concentration of interest, and a higher level of hydrostatic pressure, on the order of 0.1 kbar to 1.0 kbar, is then applied to remove gas nuclei.

As a result of the lack of cavitation inception at or near the exit port, a stream of gas-supersaturated liquid can be used to enrich a gas-deprived liquid with gas outside the high pressure reservoir simply by convection of the gas-supersaturated effluent with the gas-deprived liquid at ambient pressure. Enrichment of a gas-deprived liquid with gas by diffusion from the gas phase to the liquid is, by contrast, an extremely slow process. The lack of bubbles in the effluent additionally permits unimpeded ejection into the gas-deprived liquid. When the gas-supersaturated liquid is ejected in an air environment, the lack of cavitation inception at or near the exit port facilitates the use of the effluent in a manner similar to use of the same liquid which is not supersaturated with gas, i.e., the ejected stream remains intact, rather than becoming disintegrated into a diffuse spray near the exit port from rapid growth of gas nuclei.

Based on the teachings in the above applications and U.S. patents and the disclosure in the present application that more particularly point to certain embodiments of these teachings, the presently claimed invention provides a stabilized gas-enriched liquid produced by a process comprising the steps of:

a) preparing a mixture of gas and liquid;
b) compressing the mixture to a pressure such that the gas completely dissolves in the liquid to form a gas-enriched liquid;
c) enclosing the gas-enriched liquid within a confined space while retaining substantially the same pressure, wherein the confined space has at least one dimension less than about 0.2 mm, preferably in the range of about 0.01 micron to about 200 micron.

Alternatively, a stabilized gas-supersaturated liquid can be produced by a process comprising the steps of:

a) preparing a mixture of gas and liquid;
b) enclosing the mixture within a confined space;
c) compressing the mixture within the confined space to a pressure such that the gas completely dissolves in the liquid to form a gas-enriched liquid.

The presently claimed invention additionally provides a stabilized gas-supersaturated liquid produced by a process of steps a), b), and c), as above with the further step of d) lowering the hydrostatic pressure to a value below the dissolved gas partial pressure, within at least some portion of the space, without bubble nucleation.

The gas used in the mixture may be oxygen, nitrogen, argon, helium, carbon dioxide, ozone, and mixtures thereof. Virtually any gas may be used, as described in the above cited co-pending U.S. patent applications. As an additional example, carbon monoxide, which has a solubility in water similar to that of oxygen, could be used for the purpose of enhancing the industrial production of organic compounds by anaerobic bacteria. The liquid used in the mixture may be water, an alcohol, a ketone, an oil, a hydrocarbon, and mixtures thereof. The liquid may contain dissolved salts. A particularly preferred gas-enriched liquid is where the gas is oxygen and the liquid is an aqueous solution, such as water, saline solution or a physiological fluid. Preferably, the concentration of oxygen is in the range of 0.06 ml $O_2$ (STP)/g to 4.0 ml $O_2$ (STP)/g.

A preferred manner of enclosing the gas-enriched liquid within a confined space while retaining substantially the same pressure in the process described above is to deliver the gas-enriched liquid to a capillary tube having a hydrophilic surface and an internal diameter that retains the gas in solution and prevents formation of bubbles in the gas-enriched liquid. Alternatively, before the mixture of gas and liquid is compressed, it is delivered into such a capillary tube and then compressed such that the gas completely dissolves in the liquid to form a gas-enriched liquid within the capillary tube. The capillary tube preferably comprises glass, quartz, silica or metal. It is particularly preferred that the capillary tube be a tubing having an internal diameter of 2 to 200 microns. Another embodiment of the process for producing the gas-supersaturated liquid is to enclose the gas-enriched liquid within a porous matrix containing a plurality of capillary spaces. Such a matrix may be selected from the group consisting of porous ceramics, porous polymers, porous metals and hydrogels. The minimum spatial dimension of such spaces can range from 0.01 micron to 200 microns.

One benefit of the present invention is that a gas-supersaturated liquid produced is stable for sufficiently useful periods of time when the gas-enriched liquid is injected into a liquid environment of interest having a low concentration of the gas if the rate of flow permits mixing of the gas-enriched liquid with the environment before bubble nucleation can occur. The preferred liquid environment of interest comprises blood, water, hazardous waste material, liquid glass, a polymer, or a liquid metal. A particularly preferred embodiment is where the gas is oxygen and the liquid environment of interest is blood.

An alternative embodiment of the present invention provides a gas-supersaturated liquid produced by the process comprising the steps of:

a) preparing a mixture of gas hydrate particles and a liquid;
b) compressing the mixture so that the particles at least partially dissolve in the liquid to form a gas-enriched liquid; and
c) delivering the gas-enriched liquid while retaining substantially the same pressure to a capillary tube having an internal diameter that retains the gas in solution and prevents formation of bubbles in the gas-enriched liquid. The gas-enriched liquid may be injected into an environment of interest having a low concentration of the gas at a rate which permits mixing of the hydrate with the environment before bubble coalescence can occur.

As described in U.S. Pat. No. 5,261,875, another preferred embodiment of the present invention provides a gas-supersaturated liquid produced by the process comprising the steps of:

a) preparing a powdered gas hydrate;
b) mixing the hydrate with powdered ice which has a low concentration of the dissolved gas;
c) pulverizing the mixture of the hydrate and the ice into small particles;
d) encapsulating the mixture of the hydrate and the ice within a pressure vessel;
e) applying pressure to the mixture;
f) warming the pressure vessel and its contents to provide an aqueous suspension of the hydrate within the liquid water formed from the ice upon warming;
g) providing a conduit in communication with the pressure vessel and a catheter having one or more high resistance exit ports so that sufficient pressure is maintained for continued stabilization of the hydrate prior to emerging from the catheter; and
h) injecting the suspension of the particles into a liquid environment of interest at a rate which permits mixing of the hydrate with the environment before decomposition of the gas hydrate or bubble coalescence can occur to thereby form the gas-supersaturated liquid. The gas hydrate may be selected from the group consisting of oxygen hydrate, oxygen clathrate hydrate, and inert gas hydrate. The liquid environment of interest may be hypoxemic blood, hazardous waste material, liquid glass, a polymer, or a liquid metal.

One of the characteristic physical properties of the high-tensile strength form of water produced by a process comprising the steps of:

a) preparing gas-free water;

b) compressing the gas-free water to at least 100 bar; and c) enclosing the gas-free water within a confined space while retaining the same pressure to form the high-tensile strength form of water is that the water has a boiling point of at least above 150° C. as determined by the absence of boiling upon immersion of a loop of silica tubing 144 μm o.d., 25 μm i.d., containing the high tensile strength water, in a bath of silicone oil maintained at above 150° C., for at least 40 seconds.

A characteristic physical property of an oxygen-supersaturated form of water is the absence of bubble formation when such water contains oxygen at a partial pressure of at least 50 bar in a silica tubing having an internal diameter of 20 micron or less, and is then delivered with a minimum velocity of 2 m/sec at the distal end of said tubing into at 1 bar.

(Magnification 300×).

Figure 5:
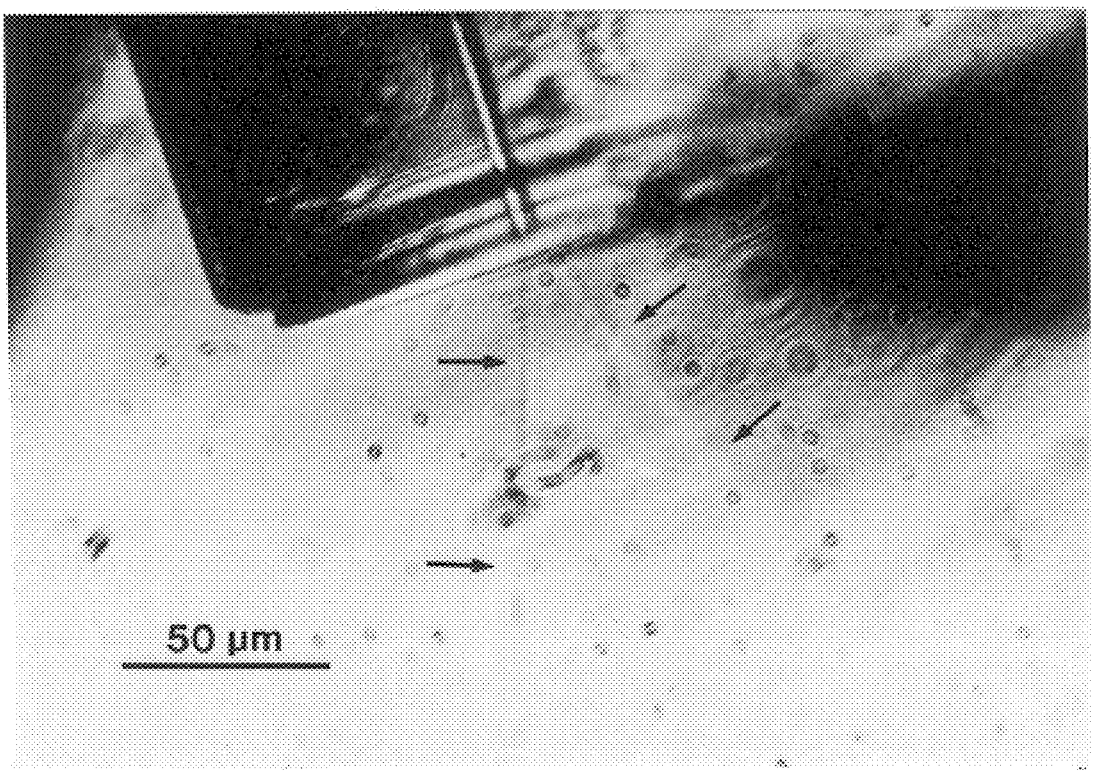

FIG. 5. Strobe light micrograph of oxygen-supersaturated (3 ml $O_2$/g [STP]) effluent from 5 μm i.d. silica capillary tube (o.d.=150 μm; 2 cm length) under water. No bubbles were observable at any location in the stream, whether conical-shaped (arrows) at relatively low velocity (<2 m/sec) or cylindrical in shape at high velocity (>20 m/sec). (Magnification 300×).

Figure 6:
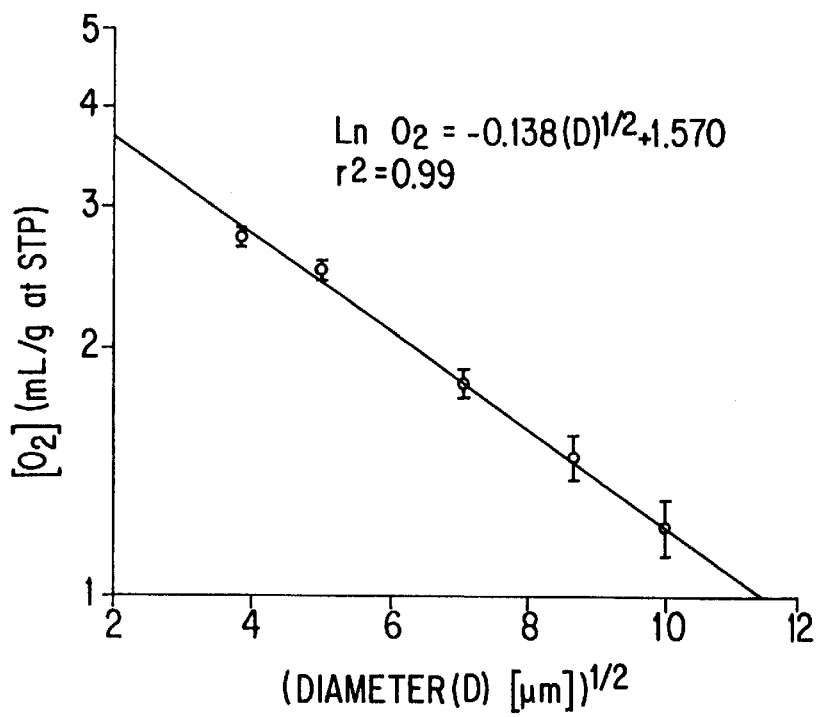

FIG. 6. Empiric relationship between the maximum oxygen concentration in $D_5W$ ([$O_2$]), plotted on a semi-logarithmic scale (ordinate), which did not result in cavitation in the effluent during infusion into water saturated with oxygen at 0.1 MPa and the square root of the i.d. (diameter) of silica tubes at the distal end of the delivery system (abscissa). The gas partial pressure was varied in 5% increments, and the maximum gas supersaturation threshold was defined as the value that was ≧5% lower than the level which resulted in at least light cavitation as determined with argon laser-induced fluorescence of fluorescein within the liquid. A nonlinear curve fit of the logarithm of the mean [$O_2$] which was stable during ejection, as a function of the capillary i.d. of the form $\log[O_2]=a_o+a_1(i.d.)^{a_2}$ resulted in a value of $a_2$ of 0.48±0.06, thereby justifying the choice of the i.d. exponent. Error bars represent ±1 s.d.

Figure 7:
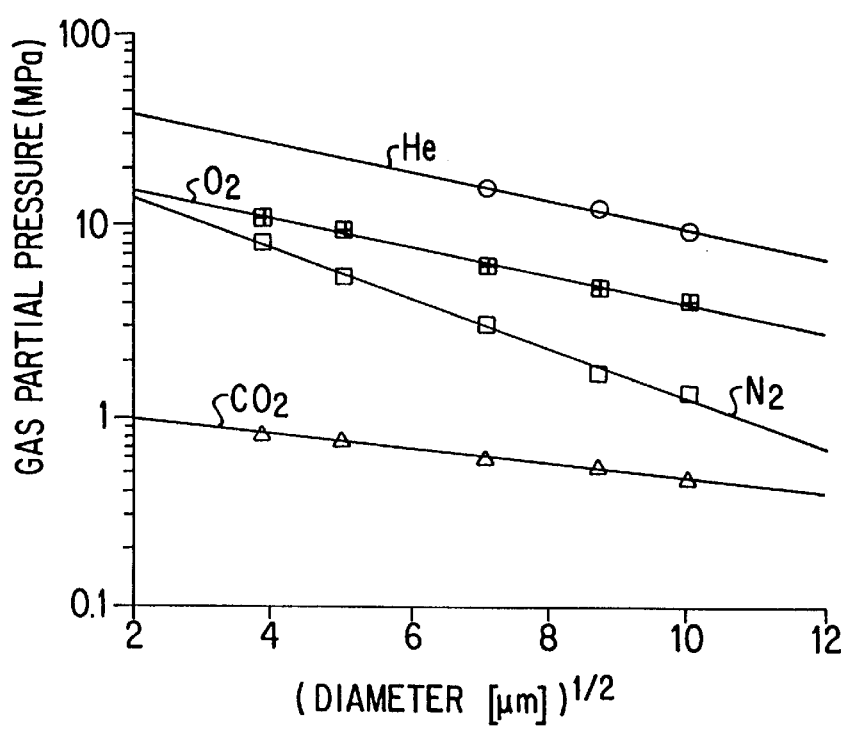

FIG. 7. Semi-logarithmic plot of the maximum gas supersaturation partial pressure in distilled water (ordinate), ≦5% below the threshold for cavitation during infusion into water at 0.1 MPa, as a function of the square root of the i.d. (diameter) of fused silica capillary tubes (abscissa). Nominal purity of each gas was >99.8% (Air Products). He=helium. $O_2$ oxygen. N2=nitrogen. $CO_2$=carbon dioxide. For each linear regression, $r^2 \geq 0.98$.

Figure 8:
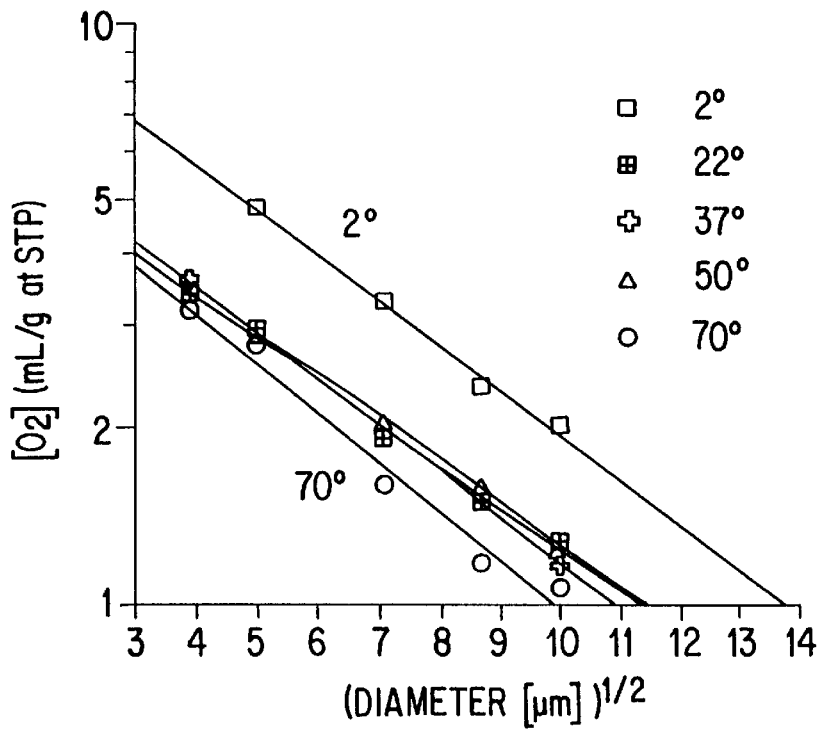

FIG. 8. Maximum oxygen partial pressure (semi-logarithmic scale) in distilled water, below the threshold for cavitation during ejection, versus the square root of the i.d. of silica capillary tubes as a function of temperature. By analysis of covariance, the slope of the 70° C. data and the y-intercept for data at 2° C. differed significantly from runs at the other temperatures (p <0.05).

Figure 9:
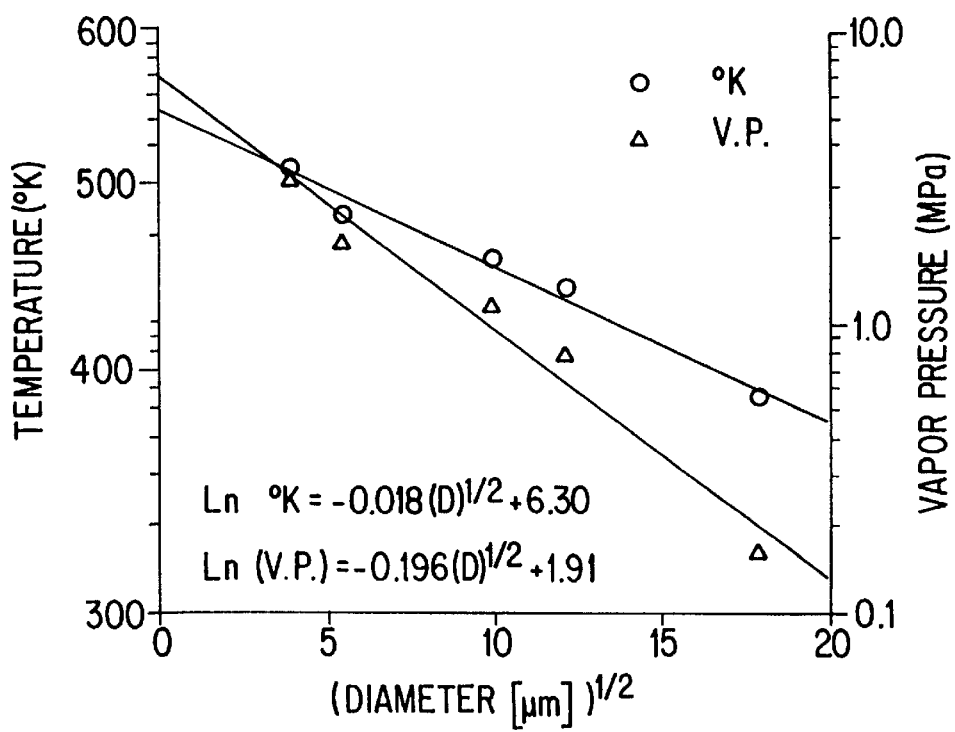

FIG. 9. Semi-logarithmic plot of maximum temperature (T) (left ordinate) and corresponding extrapolated maximum vapor pressure (V.P.; ref. 17)(right ordinate) achieved during superheating water under static conditions without boiling at 0.1 MPa within fused silica capillary tubes as a function of the square root of the i.d. (D) of the tubes (abscissa). Prior to heating, degassed water was hydrostatically compressed to 100 MPa for one min. after injection into the tube. A 15 cm long loop of each tube was immersed for 40 seconds in polydimethylsiloxane oil (Dow Corning 360 medical fluid) which was rapidly stirred with a magnetic stirrer during heating on a hot plate. Temperature measurements were performed with a glass thermometer that met ASTM E1 specifications and was calibrated before use with a thermometer having an NIST-traceable calibration certificate (Kissler Instr. Co., Westbury, N.Y.). After each immersion, light microscopy at either 100×or 400× was performed to determine whether boiling had occurred.

DESCRIPTION OF THE PREFERRED EMBODIMENTS

In the absence of cavitation nuclei, the formation of gas- or vapor-filled bubbles in water, i.e., homogeneous nucleation, requires relatively large negative pressures or high temperatures because of the inherent tensile strength of water, which may be >100 MPa (1 kbar) (J. C. Fisher, *J. Appl. Phys.* 19,1062 (1948); R. E. Apfel, *Scientific Amer.* 227, 58 (1972).). Similarly, several investigators have noted the lack of bubble formation over an observation period of many minutes upon sudden release to 0.1 MPa (1 bar) of hydrostatic pressure applied to water supersaturated with a variety of gases (E. A. Hemmingsen, *J. Appl. Phys.* 46, 213 (1975); W. A. Gerth and E. A- Hemmingsen, *Z Naturforsch* 31a, 1711 (1976); F. B. Kendrick, K. L. Wismer, and K. S. Wyatt, *J. Phys. Chem.* 28, 1308 (1924); Y. Finkelstein and A. Tamir, *AlChE J.* 31, 1409 (1985)), such as oxygen at partial pressures as high as 14 MPa, since the application of hydrostatic pressure is effective in removing cavitation nuclei. Gas-supersaturated water after decompression to 0.1 MPa is metastable, however, and mechanical disturbance of the static fluid or its enclosure results in bubble evolution, perhaps from amplification of local density gradients present at the molecular level from the thermal motion of water molecules (W. Doring, *Z Phys. Chem.* (*Leipzig*) B36, 371 (1937); ibid B38, 292 (1937); R. Furth, *Proc. Cambr. Phil. Soc.* 37, 252 (1941)). Bubble formation during ejection of gas-supersaturated water from a high pressure reservoir may additionally result from cavitation initiated within vortices associated with turbulent flow (R. B. Dean, *J. Appl. Phys.* 15, 446 (1944)).

Figure 1A:
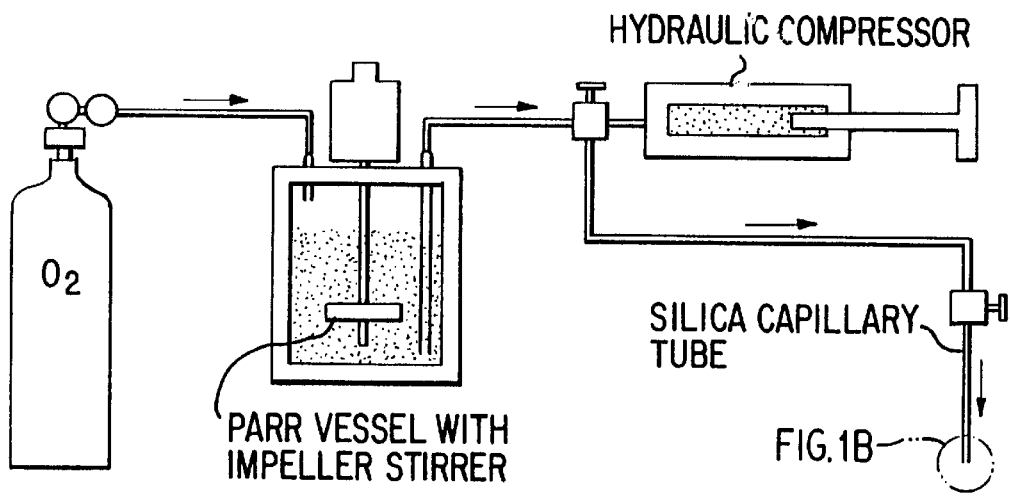
FIG. 1. Schematic of experimental apparatus used to prepare oxygen-supersaturated water. Either distilled water (Sybron Barnstead) or a physiologic solution (0.9 g % NaCl [NS] or 5 g % dextrose in water [$D_5W$]), after degassing in a vacuum, was rapidly stirred for at least an hour in a 300 ml Parr reactor vessel with an impeller stirrer at 1600 rpm under pressure (17 to 150 MPa) with oxygen from a medical grade oxygen cylinder (Air Products; nominal purity >99.8%). The oxygenated liquid was transferred to a hydraulic compressor (model HC-60, Leco/Tem-Press Div. or model 50-6-30, High Pressure Equipment Co.) for application of 100 MPa pressure for at least one minute. The fluid was then delivered initially at 100 MPa through a fused silica capillary tube (Polymicro Technologies) having an i.d. of 15–100 μm (tolerance ±1 μm). For some runs, the distal end of a silica tube was drawn in a propane torch and cleaved to provide a distal tapered section having an i.d. of 3–10 μm (videomicroscopy at 1000×magnification) over a few millimeters at the exit port. By adjusting the length of 5 non-tapered tubes over a 0.23 m–10.0 m range in proportion to the i.d. (15–100 μm) squared, the flow velocity of water through each tube (range =0.04 to 1.6 ml/min.) was the same for a given hydrostatic pressure (e.g., 3.5 m/sec. at 100 MPa).
Figure 1B:
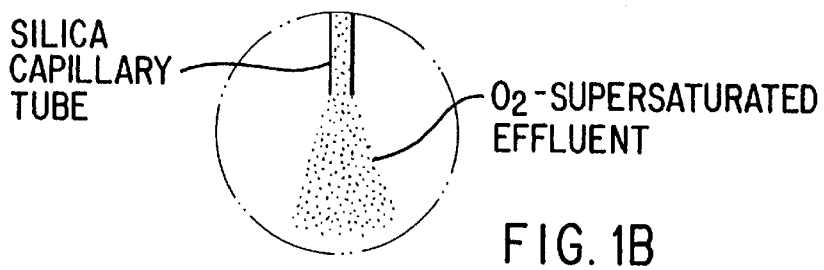
Figure 2:
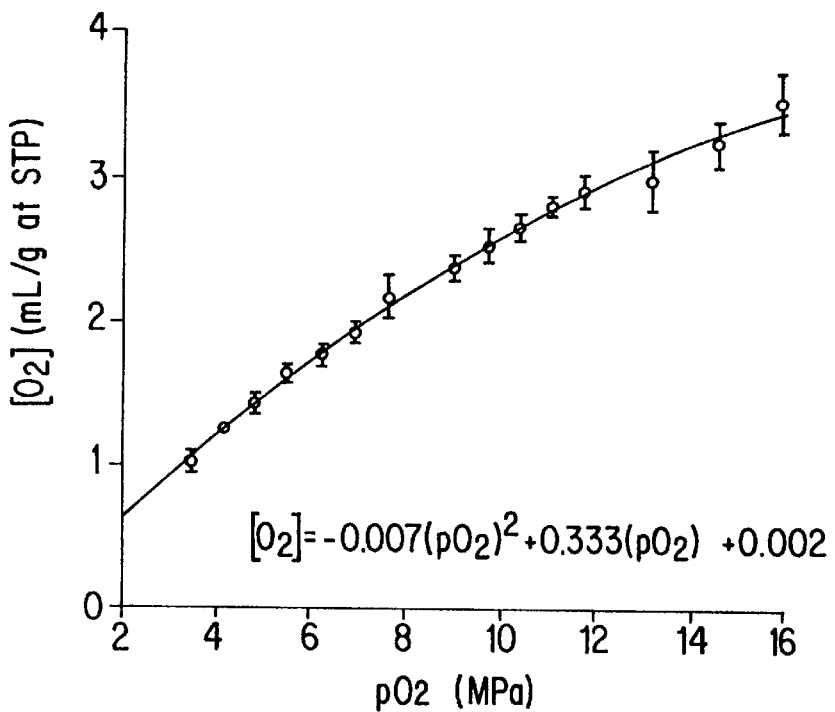
FIG. 2. Relationship between $pO_2$ and dissolved oxygen concentration ([$O_2$]) in water at 22° C. The measured oxygen concentration in water, over a 3.4–15.3 MPa range, deviates slightly from Henry's law. Error bars represent ±1 s.d.

The present invention provides a novel method of producing a new stabilized form of oxygen-supersaturated water and a novel method of infusing this oxygen-supersaturated water into aqueous media at 0.1 MPa without bubble formation in the effluent (J. R. Spears, U.S. Pat. No. 5,407,426 (1995)). Distilled water or a physiologic solution (0.9 g % NaCl [NS] or 5 g % dextrose in water [$D_5W$]) was saturated with oxygen at a partial pressure of 1.7 to 15 MPa in a Parr reactor vessel (FIGS. 1, 2). Further hydrostatic compression of the liquid to 100 MPa, after saturation at the desired oxygen partial pressure of interest, was achieved in a high pressure vessel with a hydraulic pump. The liquid was then delivered at 70–100 MPa to the proximal end of one or more silica or glass capillary tubes having an i.d. of 3 to 100 $\mu$m, after flushing the tubes for one minute with degassed, distilled water at 100 MPa. The concentration of oxygen in the ejected gas-supersaturated water was found to agree well with that reported by others under similar high oxygen partial pressures.

Ejection of 1 ml of $O_2$-supersaturated water into an air-filled pipette (mercury column at 0.1 MPa) through a silica tube resulted in >90% decomposition as estimated by measurement of the $pO_2$ in the residual liquid. The remaining dissolved oxygen was measured after brief sonication. The volume of gas liberated from all liquid samples described herein is expressed as ml/g under conditions (295° K, 0.1 MPa) which approximate STP. Evaluation of the rate of oxygenation of a 200 ml volume of water within the 300 ml capacity Parr vessel pressurized with oxygen at 7.5 MPa demonstrated that 95% of the equilibrium value at 295° K (3 days) was obtained at 30 min. and 100% at 45 min. All runs were therefore performed on samples equilibrated with a gas for at least 1 hr. The solubility of oxygen in water under a wide variety of conditions has been compiled in *Oxygen & Ozone, Solubility Data Series*, R. Battino, ed. (Pergammon Press, New York, 1981), vol.7. In one relevant study, O. L. McKee, Jr. (PhD thesis, Purdue University, 1953) found that the oxygen concentration in water at 10 MPa and 0° C. (3.93 ml $O_2$/g at STP) was 27% lower than the value predicted by Henry's law.

1. Confirmation of Bubble Absence.

Figure 3:
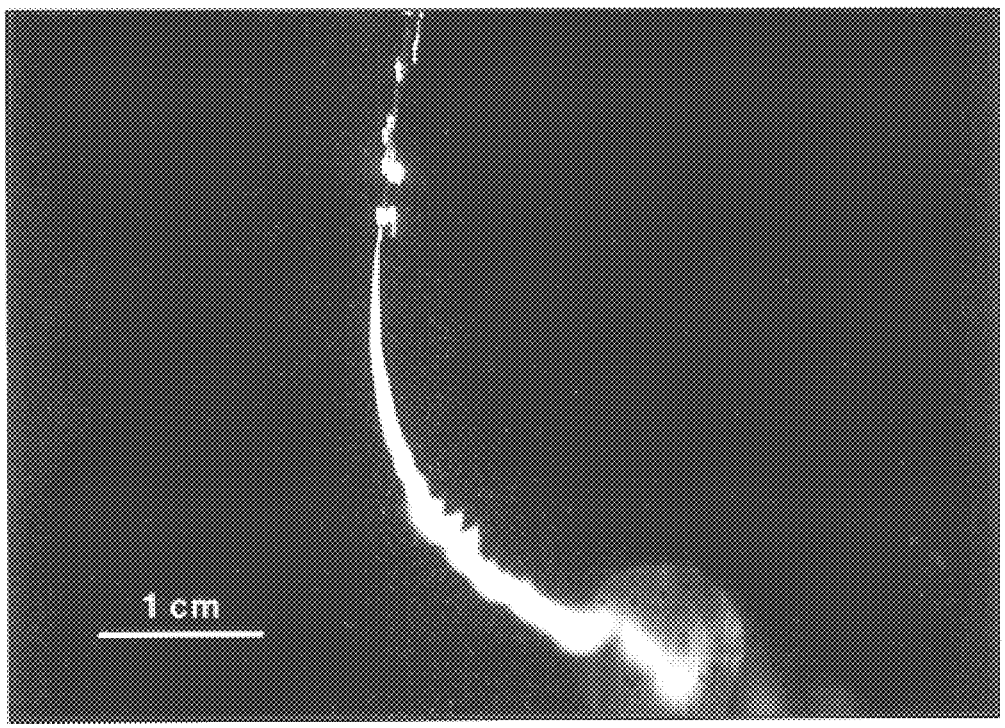
FIG. 3. Injection of $O_2$-supersaturated water (3 ml $O_2$/g [STP]) containing fluorescein (Sigma) through a 2 cm long segment of a 35 parallel channel (3 (μm/channel) borosilicate tube (80 μm o.d.), pressurized to 70 MPa, into water saturated with oxygen at 0.1 MPa was not associated with bubble formation in the effluent at any time for the entire volume in the pressure vessel. Argon laser-induced (488/515 nm, model 164, Spectra-Physics, Mountain View, Calif.) fluorescence of the dye was used to visualize the stream.

The complete absence of bubble formation in transilluminated, grossly stabilized effluent during infusion of oxygen-supersaturated water into aqueous media was confirmed by four independent methods. Fiberoptically delivered 488/515 nm light from an argon-ion laser was used to visualize fluorescein within a stream of $D_5W$ ejected into tapwater or plasma from individual silica tubes having an i.d. <10 $\mu$m over a 1 to 50 mm length at the distal end. All eddies of the effluent, which had an $O_2$ content of 3 ml/g (STP), appeared bubble-free and slightly denser than water in all runs (n>50). A similar observation (n=4) was made for a 35 parallel channel borosilicate glass tube (2 cm long segments; o.d. 80 $\mu$m) having a mean channel i.d. of 3 $\mu$m (FIG. 3). Neither vigorous movement of any tube nor entrainment by the stream of preexisting bubbles, already present in the beaker, altered its stability.

Bubble formation in the effluent was evident under certain conditions. Partial obstruction of a capillary lumen by a solid contaminant; marked disturbance of effluent outflow by direct placement of the exit port against a solid surface; or ejection into a confined space which prevented rapid dilution resulted in prominent gas nucleation. In addition, after initiation of bubble-free flow at 100 MPa, lowering the hydrostatic pressure to levels below the dissolved gas partial pressure frequently resulted in bubble formation. Perhaps most noteworthy, there was an inverse relationship between the maximum concentration of oxygen which could be stabilized during ejection and the i.d. of the tube.

Figure 4:
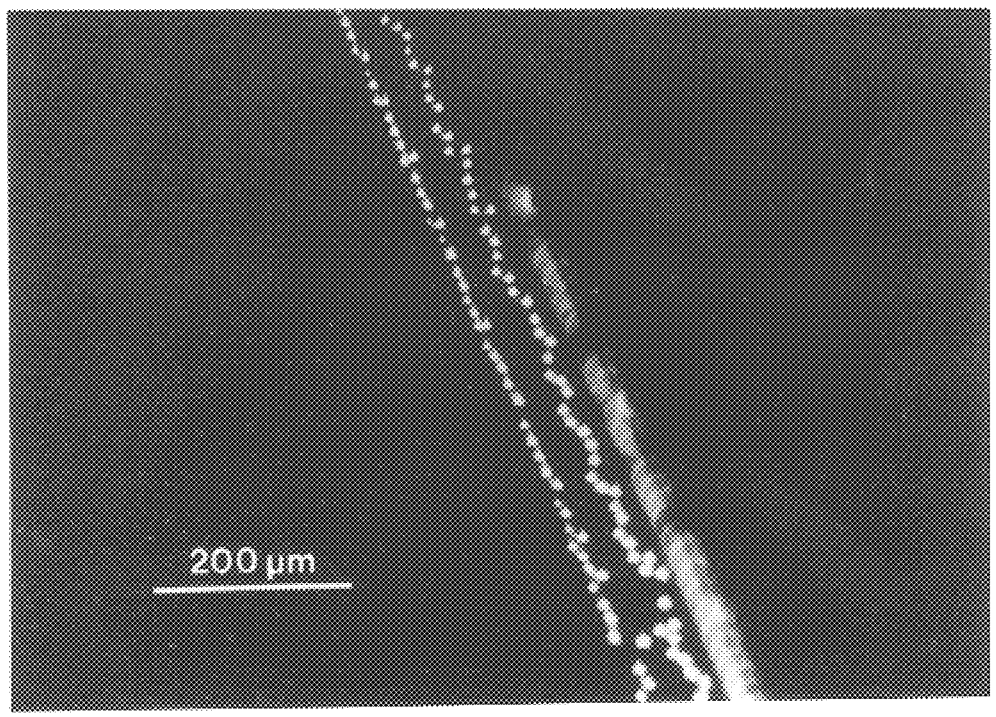
FIG. 4. Photomicrograph of 20 ns strobe light exposure (model 437 B high intensity nanopulse system, Xenon, Woburn, Mass.) of an unstable oxygen-supersaturated $D_5W$ stream (8 μm i.d. silica capillary tube, 4 ml $O_2$/g [STP]), within which bubble growth occurs in 3 columns (one out of focal plane) distal to the exit port, under water saturated with oxygen.

Because the relatively rapid velocity (2–20 m/sec) of the effluent precluded temporal resolution of potential bubbles with conventional light microscopy, the effluent was observed in water with a 20 ns ($10^{-9}$ sec.) strobe light through a light microscope (FIGS. 4,5). No bubbles were present in the effluent at a dissolved oxygen concentration of 3 MI $O_2$/g, when the i.d. of distal end of the silica tube was 3–6 $\mu$m (n=20). In contrast, one to three columns of bubbles distal to the exit port of larger bore tubes were noted at the same oxygen concentration.

To evaluate the possibility that bubbles smaller than the spatial resolution of the microscope were present transiently, effluent containing 3 ml $O_2$/g from either a 3 to 6 $\mu$m i.d. silica tube or a 35 parallel channel tube (3 $\mu$m i.d./channel) was injected into either dog or rabbit plasma (n=12) or a 5 g % human serum albumin solution (n=8) within a cuvette, and the particle/bubble size distribution within the liquid was determined before and either during or immediately after 3–5 min. infusions with a submicron multi-angle particle size analyzer (Coulter model N4 MD). No evidence of bubbles was found in any run.

In order to determine whether infusion of an oxygen-supersaturated physiologic solution into blood could be performed without bubble formation, oxygen-supersaturated $D_5W$ (3 ml $O_2$/g) was injected in vitro into 10–20 ml aliquots of citrated venous dog blood from a 30 $\mu$m i.d. silica tube for periods sufficient to increase oxygen saturation to 100% during continuous $pO_2$ monitoring and slow mixing with a magnetic stirrer. Blood $pO_2$ was continuously monitored with an oxygen microelectrode (model 768-20R, Diamond General, Ann Arbor, Mich.) that was calibrated against an Instrumentation Laboratories (model 1312) blood gas analyzer. As a control, bolus injection of 0.1 ml of a translucent albumin solution, several minutes after sonication to produce stable microbubbles (M. W. Keller, S. S. Segal, S. Kaul, and B. Duling. *Circ. Res.* 65, 1 (1989)), into 3 blood samples produced a bright echogenic cloud of bubbles. No bubbles were observed during infusions of oxygen-supersaturated $D_5W$ up to a $pO_2$ of at least 0.04 MPa (300 mmHg) by ultrasound imaging (n=21)(3.5 MHz transducer, J & J lrex PS ultrasonic imaging system). Continuous bubble generation was noted at a mean threshold $pO_2$ of 0.12±0.05 MPa (±1 s.d.) (830±380 mmHg). Plasma hemoglobin, determined spectrophoto metrically (W. G. Zijlstra, A. Buursma, and A. Zwart. *J. Appl. Physiol.* 54, 1281 (1983)) immediately after completion of the injection in additional runs (n=19), wherein a minimum $pO_2$ of at least 0.04 MPa was achieved in all samples, was compared to control samples (n=9). The flow velocity used (approximately 2 m/sec) was below the known threshold for hemolysis (L. Crum. *Nature* (London) 278, 148 (1979)). No increase in plasma hemoglobin was observed (p>0.05, unpaired Student's t-test).

2. Maximum Stabilized Gas-supersaturation Level vs. Capillary i.d.

The relationship between the maximum concentration of oxygen in distilled water (after transient hydrostatic compression to 100 MPa), which is unassociated with cavitation inception in the effluent, as visualized with the aid of fluorescein, during ejection into tapwater at 0.1 MPa and the i.d. of silica capillary tubing was defined over a 15–100 μm diameter range (FIG. 6). The maximum partial pressure of helium, nitrogen, and carbon dioxide in distilled water, below the threshold for bubble nucleation during ejection was similarly determined (FIG. 7). Under the conditions of the study, an inverse linear relationship was found between the logarithm of either the gas concentration or the partial pressure and the square root of the i.d. of the capillary tube. A maximum dissolved oxygen partial pressure of 14.4 MPa, extrapolated to a 5 μm i.d. silica tube (22° C.), is similar to the maximum supersaturation threshold oxygen tension in water under static conditions (E. A.

Hemmingsen, *J. Appl. Phys.* 46, 213 (1975)). Likewise, the markedly higher partial pressure threshold noted for helium is similar to that observed by Hemmingsen. Since such thresholds, under static conditions, are dependent more on gas concentration than on partial pressure, it is not surprising that the partial pressure threshold for carbon dioxide was found to be considerably lower than those of the other gases studied.

The length of silica tubes did not appear to significantly affect the maximum oxygen partial pressure in water that was stable during ejection. For example, a plot of this variable against 8 different tube lengths over a 0.6 m-36 m range for a 50 μm i.d silica tube yielded a linear regression slope of <0.1 Mpa/m ($r^2$<0.1).

In contrast to results obtained with silica tubes, when hollow carbon fibers with a 5 μm i.d. (2–5 cm in length) were used to terminate the distal end of a silica tube, no runs were successful at injecting $D_5W$ with 3 ml $O_2$/g, pressurized to 100 MPa, into water at ambient pressure without bubble formation. A possible explanation for the difference in the results obtained with the carbon and silica tubes is that the former present a hydrophobic surface. By analogy, hydrophobic impurities have been implicated as sources of cavitation nuclei (L. Crum. *Nature* (London) 278, 148 (1979)). Channels fabricated from some alternative materials, however, do appear suitable for stabilizing gas-supersaturated liquids. For example, the maximum oxygen concentration in water that is stable during ejection through a 177 μm i.d. 316 stainless steel tube (1 m long) was found to be within 5% of the value predicted from the regression equation derived for silica tubes (FIG. 6).

3. Effects of Other Variables.

A number of factors are known to alter the cavitation threshold of water, such as temperature, presence of electrolytes, and surface tension, in addition to dissolved gas tension. There was little effect of temperature over a 22° C. to 50° C. range on the maximum threshold oxygen partial pressure, but a markedly higher threshold at 2° C. and a lower one at 70° C. (FIG. 8). These observations are similar to the behavior of argon and nitrogen supersaturated solutions under static conditions (E. A. Hemmingsen, *J. Appl. Phys.* 46, 213 (1975)). The results for normal saline at 22° C. were nearly identical to those for distilled water at the same temperature (5% mean difference for 5 silica tubes 15–100 μm i.d.; p=0.9, unpaired t-test).

A variety of physical properties (viscosity, surface tension, etc.) of the medium into which gas-supersaturated water is injected also may affect the stability of the effluent. However, infusion of a hydrostatically compressed (100 MPa) stream of water supersaturated with oxygen at 6 MPa from a 50 μm i.d. silica capillary tube at 2 m/sec into test tubes (1 cm diameter) containing a miscible liquid, including either ethanol, acetone, or ethylene glycol, was unassociated with bubble formation in the effluent. Similarly, ethanol and acetone could be supersaturated with oxygen at 5 MPa and, after 100 MPa hydrostatic compression, infused into miscible liquids at 0.1 MPa through a 50 μm silica capillary tube at 2 m/sec without effluent instability. Thus, although additional studies will be required to define the potential effect of viscosity and surface tension on the stability of gas-supersaturated liquids, the influence of variations in these properties appears to be relatively minor.

A potentially relevant relationship was noted between the maximum temperature achieved in superheated water under static conditions at 0.1 MPa within fused silica capillary tubes as a function of the i.d. of the tubes (FIG. 9). Pretreatment with hydrostatic compression to 100 MPa, very likely, increased the tensile strength of the water. Several groups have reported superheating water at 0.1 MPa to a maximum temperature of 260° C. to 280° C. for a few seconds, either with water droplets suspended in an immiscible fluid or within freshly drawn capillary tubes (R. E. Apfel, *Nature Phys. Science* 238, 63 (1972); L. J. Briggs, *J. Appl. Phys.* 26, 1001 (1955); M. Blander, D. Hengstenberg, and J. Katz, *J. Phys. Chem.* 75, 3613 (1971). In contrast to the effect of capillary dimensions on maximum superheating temperatures, no such effect was noted on maximum supercooling temperatures (261°–262° K for all silica tubes having an i.d. of 15 to 100 μm) of distilled water above the freezing point at 0.1 MPa after 100 MPa hydrostatic compression.

The freezing point of distilled water at 0.1 MPa within five silica capillary tubes 15–100 gm in i.d. was determined after hydrostatic compression to 100 MPa for 1 min. A 20 cm loop of tubing was immersed for 5 min. in a temperature controlled bath (model 9000, Allied/Fisher Scientific). The maximum supercooling temperature of water, below the freezing point, was either 261° or 262° K for all tubes. The use of capillary tubes to supercool water to considerably lower levels is well known, as summarized by C. A. Angell, *Ann. Rev. Phys. Chem.* 34, 593 (1983).

Without wishing to be bound by theory, I believe that the stability conferred by small diameter tubes during ejection of gas-supersaturated water may result from a combination of effects. First, sites for heterogeneous nucleation within water and along the surface of a hydrophilic material such as silica are eliminated by the application of a high hydrostatic pressure which also, very likely, contributes to increased stability during superheating. Second, maintenance of a hydrostatic pressure which exceeds the dissolved gas partial pressure along the length of the capillary tube, except for a relatively short distal section close to the exit port, reduces the time available for bubble nucleation. By analogy, elimination of cavitation nuclei by careful filtration has been shown by others to increase the threshold for heterogeneous nucleation to 16 MPa and to even higher levels (20 MPa) for brief periods of time, on the order of a few seconds (M. Greenspan and C. Tschiegg, *J. Res. Natl. Bur. Stds.* 71C, 299 (1967)). After ejection, the supersaturated fluid is mixed with the surrounding fluid, rapidly diluted, and the resultant much lower dissolved gas partial pressure is insufficient to initiate cavitation. Additionally, the combination of a high hydrostatic pressure and a confined space very likely produces a "film" that dewets with great difficulty from the solid surface (thereby producing a gas nucleus for heterogeneous nucleation), in view of the relatively small force generated by a thin column of liquid. The possibility also exists that the structure of water, upon application of a high hydrostatic pressure within a confined space, is altered to confer increased stability; the presence of a high concentration of a gas may also alter the water structure to confer stability in a manner similar to effect of the presence of a gas facilitating the formation of stable clathrate hydrate structures.

The results of the application of the present invention demonstrate that oxygenation of aqueous media, including blood, with oxygen-supersaturated solutions, without bubble nucleation in the effluent, is feasible. The rate of oxygenation of an aqueous medium by this approach appears to be limited only by the rate of liquid convection, a relatively rapid process compared to diffusion at a gas-liquid interface. Methods for fabrication of large arrays of parallel microchannels within glass substrates are well developed, so that much greater flow rates of stabilized gas-supersaturated liquids are achievable.

In addition to the use of stabilized, gas-enriched liquids, there are potentially many applications of stabilized liquids that are not gas-enriched. For example, cavitation occurs at a low threshold in ordinary water in many scientific fields, such as in detectors in particle physics, around propellers in ship engineering, and in association with other moving objects such as rapidly spinning burrs and ultrasonic horns. The use of the present method to increase the threshold for cavitation in liquids by ejection into a relevant environment should be apparent.

Although the present invention has been described and illustrated in detail, it is clearly understood that the same is by way of illustration and example only and is not to be taken by way of limitation, the spirit and scope of the present invention being limited only by the terms of the appended claims.

All references cited in the present specification are incorporated by reference.

What is claimed is:

1. A process for preparing and delivering a gas-enriched liquid comprising the steps of:
   a) preparing a mixture of gas and liquid;
   b) compressing the mixture to a pressure such that the gas completely dissolves in the liquid to form a gas-enriched liquid;
   c) enclosing the gas-enriched liquid within a confined space while retaining substantially the same pressure, wherein the confined space has at least one dimension less than about 0.2 mm and said confined space has at least one exit opening to a fluid or gas environment site of interest having a lower pressure than of the pressure of the confined space; and
   d) delivering the gas-enriched liquid from the confined space out through the at least one exit opening to the lower pressure environment without formation of bubbles.

2. The process according to claim 1 wherein the confined space has at least one dimension in the range of about 0.01 micron to about 200 micron.

3. The process of claim 1 wherein the gas is selected from the group consisting of oxygen, nitrogen, argon, helium, carbon monoxide, carbon dioxide, ozone, and mixtures thereof.

4. The process of claim 1 wherein step c) comprises delivering the gas-enriched liquid to a capillary tube having a hydrophilic surface and an internal diameter that retains the gas in solution and prevents formation of bubbles in the gas-enriched liquid.

5. The process of claim 1 wherein the confined space is within a tubing having an internal diameter of 2 microns to 200 microns, wherein the tubing is glass, silica, quartz, a polymer, or metal.

6. The process according to claim 1 wherein said liquid is supersaturated by delivery to the site of interest wherein the fluid or gas environment is at a pressure below the dissolved gas partial pressure of said gas-enriched liquid, without bubble nucleation.

7. The process of claim 1 wherein the liquid is selected from the group consisting of water, alcohols, ketones, oils, hydrocarbons, and mixtures thereof.

8. The process of claim 7 wherein the liquid contains dissolved salts.

9. The process of claim 1 wherein the gas is oxygen and the liquid is water.

10. The process of claim 9 wherein the water contains oxygen at a concentration in a range of 0.06 ml (STP)/g to 4.0 ml (STP)/g.

11. The process of claim 1 wherein the confined space is within a porous matrix containing a plurality of capillary spaces.

12. The process of claim 11 wherein the confined space is selected from the group consisting of porous ceramics, porous polymers, porous metals and hydrogels.

13. The process according to claim 1 wherein the site of interest is a liquid environment of interest having a lower concentration of the, gas at a rate which permits mixing of the gas-enriched liquid with the environment before bubble nucleation in the effluent can occur.

14. The gas process according to claim 13 wherein the liquid environment of interest comprises blood, hazardous or biological waste material, liquid glass, a liquid polymer, or a liquid metal.

15. The process according to claim 14, wherein the gas is oxygen and the liquid environment of interest is blood.

16. A process for preparing and delivering a gas-enriched liquid comprising the steps, of:
   a) preparing a mixture of gas and liquid;
   b) enclosing the mixture within a confined space;
   c) compressing the mixture within the confined space to a pressure such that the gas completely dissolves in the liquid to form a gas-enriched liquid, wherein the confined space has at least one dimension less than about 0.2 mm; and
   d) delivering the gas-enriched liquid from the confined space through at least one exit opening having a dimension less than about 0.2 mm that is open to a lower pressure environment without bubble formation.

17. The process according to claim 16 wherein the confined space has at least one dimension in the range of about 0.01 micron to about 200 micron.

18. The process of claim 16 wherein the gas is selected from the group consisting of oxygen, nitrogen, argon, helium, carbon monoxide, carbon dioxide, ozone, and mixtures thereof.

19. The process of claim 16 wherein the liquid is selected from the group consisting of water, alcohols, ketones, oils, liquid hydrocarbons, and mixtures thereof.

20. The process of claim 16 wherein the gas is oxygen and the liquid is water.

21. The process of claim 16 wherein step b) comprises delivering the mixture to a capillary tube having a hydrophilic surface and an internal diameter that upon compressing the mixture in step c) retains the gas in solution and prevents formation of bubbles in the gas-enriched liquid.

22. The process of claim 16 wherein the confined space is within a tubing having an internal diameter of 2 microns to 200 microns, wherein the tubing is glass, silica, quartz or metal.

23. The process according to claim 16 wherein said liquid is supersaturated by delivery to the site of interest wherein the fluid or gas environment is at a pressure below the dissolved gas partial pressure of said gas-enriched liquid, without bubble nucleation.

24. The process of claim 16 wherein the liquid contains dissolved salts.

25. The process of claim 24 wherein the water contains oxygen at a concentration in the range of 0.06 ml (STP)/g to 4.0 ml (STP)/g.

26. The process of claim 16 wherein the confined space is within a porous matrix containing a plurality of capillary spaces.

27. The process of claim 26 wherein the confined space is selected from the group consisting of porous ceramics, porous polymers, porous metals, and hydrogels.

28. The process, as set forth in claim 16, wherein the gas-enriched fluid is supersaturated.

29. The process, as set forth in claim 16, wherein the at least one exit opening comprises an internal dimension less than about 0.2 mm.

30. A process for preparing and delivering a gas-enriched liquid comprising the steps of:
   a) preparing a mixture of gas and liquid;
   b) compressing the mixture to a pressure such that the gas completely dissolves in the liquid to form a gas-enriched liquid;
   c) delivering the gas-enriched liquid in a bubble-free manner through a delivery device to a site having a lower pressure, the delivery device having at least one exit opening and a dimension less than about 0.2 mm.

31. The process, as set forth in claim 30, wherein the gas comprises one of oxygen, nitrogen, argon, helium, carbon monoxide, carbon dioxide, ozone, and mixtures thereof.

32. The process, as set forth in claim 30, wherein step c) comprises delivering the gas-enriched liquid through a capillary tube having a hydrophilic surface and an internal diameter that retains the gas in solution and prevents formation of bubbles in the gas-enriched liquid.

33. The process, as set forth in claim 30, wherein step c) comprises delivering the gas-enriched liquid through a tube having an internal diameter between about 2 microns and about 200 microns, wherein the tubing comprises one of glass, silica, quartz, a polymer, and metal.

34. The process, as set forth in claim 30, wherein step b) comprises gas supersaturating the liquid.

35. The process, as set forth in claim 30, wherein the liquid comprises one of water, alcohols, ketones, oils, hydrocarbons, and mixtures thereof.

36. The process, as set forth in claim 30, wherein the gas comprises oxygen and wherein the liquid comprises water.

37. The process, as set forth in claim 36, wherein step b) comprises forming the gas-enriched liquid wherein the water contains the oxygen at a concentration in a range of 0.06 ml (STP)/g to 1 ml (STP)/g.

38. The process, as set forth in claim 30, wherein step b) comprises compressing the mixture within a porous matrix containing a plurality of capillary spaces.

39. The process, as set forth in claim 38, wherein the porous matrix comprises one of porous ceramics, porous polymers, porous metals and hydrogels.

40. The process, as set forth in claim 30, wherein the site comprises a liquid environment having a lower concentration of the gas, and wherein the gas-enriched liquid is delivered at a rate Which permits mixing of the gas-enriched liquid with the liquid environment without bubble nucleation.

41. The process, as set forth in claim 40, wherein the liquid environment comprises one of blood, hazardous or biologic waste material, liquid glass, a liquid polymer, and a liquid metal.

42. A process for preparing and delivering a gas-enriched liquid comprising the steps of:
   a) disposing a gas and a liquid within a member having an exit opening and at least one internal dimension being less than about 0.2 mm;
   b) compressing the gas and the liquid within the member to a pressure such that the gas completely dissolves in the liquid to form a gas-enriched liquid; and
   c) delivering the gas-enriched liquid from the member through the exit opening to a lower pressure environment without bubble formation.

43. The process, as set forth in claim 42, wherein the gas comprises one of oxygen, nitrogen, argon, helium, carbon monoxide, carbon dioxide, ozone, and mixtures thereof.

44. The process, as set forth in claim 42, wherein step c) comprises delivering the gas-enriched liquid through a capillary tube having a hydrophilic surface and an internal diameter that retains the gas in solution and prevents formation of bubbles in the gas-enriched liquid.

45. The process, as set forth in claim 42, wherein step c) comprises delivering the gas-enriched liquid through a tube having an internal diameter between about 2 microns and about 200 microns, wherein the tubing comprises one of glass, silica, quartz, a polymer, and metal.

46. The process, as set forth in claim 42, wherein step b) comprises gas supersaturating the liquid.

47. The process, as set forth in claim 42, wherein the liquid comprises one of water, alcohols, ketones, oils, hydrocarbons, and mixtures thereof.

48. The process, as set forth in claim 42, wherein the gas comprises oxygen and wherein the liquid comprises water.

49. The process, as set forth in claim 48, wherein step b) comprises forming the gas-enriched liquid wherein the water contains the oxygen at a concentration in a range of 0.06 ml (STP)/g to 4.0 ml (STP)/g.

50. The process, as set forth in claim 42, wherein step b) comprises compressing the mixture within a porous matrix containing a plurality of capillary spaces.

51. The process, as set forth in claim 50, wherein the porous matrix comprises one of porous ceramics, porous polymers, porous metals and hydrogels.

52. The process, as set forth in claim 42, wherein the lower pressure environment comprises a liquid environment having a lower concentration of the gas, and wherein the gas-enriched liquid is delivered at a rate which permits mixing of the gas-enriched liquid with the liquid environment without bubble nucleation.

* * * * *